United States Patent [19]

Tagawa et al.

[11] Patent Number: 4,778,891

[45] Date of Patent: Oct. 18, 1988

[54] CERTAIN PYRANO (3,4-F)-INDOLIZINE DERIVATIVES

[75] Inventors: Hiroaki Tagawa; Hirofumi Terasawa; Akio Ejima, all of Tokyo, Japan

[73] Assignees: Daiichi Seiyaku Co., Ltd.; Kabushiki Kaisha Yakult Honsha, both of Tokyo, Japan

[21] Appl. No.: 919,388

[22] Filed: Oct. 16, 1986

[30] Foreign Application Priority Data

Oct. 21, 1985 [JP] Japan ............................ 60-233366
Dec. 25, 1985 [JP] Japan ............................ 60-296127
Aug. 20, 1986 [JP] Japan ............................ 61-194821
Aug. 20, 1986 [JP] Japan ............................ 61-194822

[51] Int. Cl.$^4$ ................... C07D 491/14; C07D 491/20
[52] U.S. Cl. ......................................... 546/18; 546/116; 546/92
[58] Field of Search ................................. 546/92, 18

[56] References Cited

PUBLICATIONS

Wani et al., Chem. Abstracts, vol. 93, (3) abst. No. 93:26609a Jul. 21, 1980.
Wani et al., Chem. Abstracts, vol. 105, (7) abst. No. 105:57922t Aug. 18, 1986.
Wani et al., Journal of Med. Chem. vol. 29(8), pp. 1553–1555 (1986).

*Primary Examiner*—Alan L. Rotman
*Attorney, Agent, or Firm*—Oblon, Fisher, Spivak, McClelland & Maier

[57] ABSTRACT

A pyranoindolizine derivative represented by the following general formula (I):

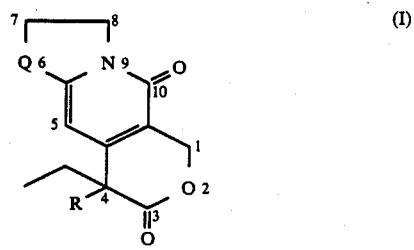

wherein R means a hydrogen atom or hydroxyl group and Q denotes >C=O or

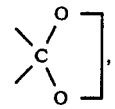

with a proviso that Q is other than >C=O when R is a hydrogen atom. Its preparation process is also described.

3 Claims, No Drawings

CERTAIN PYRANO (3,4-F)-INDOLIZINE DERIVATIVES

BACKGROUND OF THE INVENTION

1. Field of the Invention

This invention relates to novel pyranoindolizine derivatives, and more specifically to pyranoindolizine derivatives which are useful as intermediates for the synthesis of camptothecin derivatives having anticancer effects and are represented by the following formula (I):

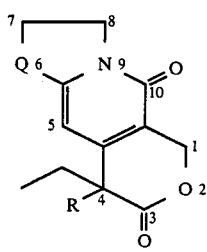

wherein R means a hydrogen atom or hydroxyl group and Q denotes >C=O or

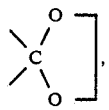

with a proviso that Q is other than >C=O when R is a hydrogen atom.

2. Description of the Prior Art

Camptothecin derivatives represented by the following formula (II) or (III) have conventionally been known to have excellent anticancer effects [Japanese Patent Laid-Open No. 39683/1983; Tetrahedron 37, 1047(1981)]:

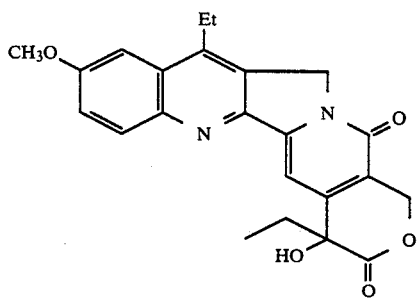

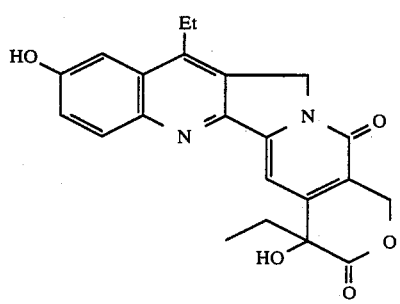

It has hence been desired to provide synthetic intermediates suitable for use in the advantageous synthesis of the derivatives.

On the other hand, natural camptothecin represented by the following formula (IV*):

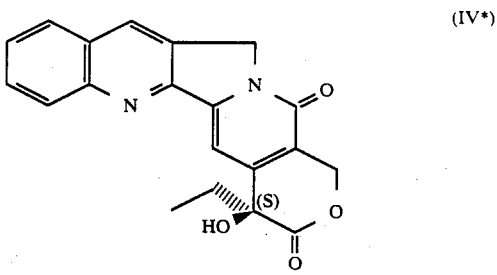

has been known to have the S-configuration at the 20 l-position thereof. It has therefore been desired to provide synthetic intermediates which permit advantageous preparation of natural camptothecin having the S-configuration and its derivatives.

SUMMARY OF THE INVENTION

The present inventor has conducted various researches with a view toward preparing such camptothecin derivatives advantageously. As a result, it has been found that the above-mentioned camptothecin derivatives can be advantageously derived on an industrial scale from pyranoindolizine derivatives which have the formula (I) and have now been synthesized for the first time by the present inventor, leading to completion of this invention.

It has also been found that natural camptothecin can be readily derived from a pyranoindolizine derivative, which has the S-configuration at the 4-position and is represented by the following formula (I*):

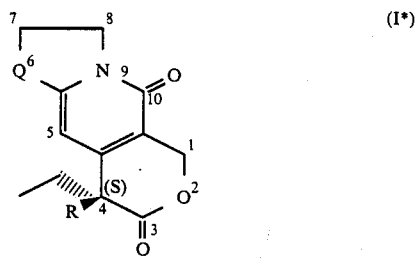

wherein Q and R have the same meaning as defined above, out of the compounds (I).

Accordingly, an object of this invention is to provide pyranoindolizine derivatives which are represented by the above formula (I) and are useful as intermediates for the synthesis of antitumor substances.

Another object of this invention is to provide a pyranoindolizine derivative represented by the above formula (I*).

A further object of this invention is to provide a process for the preparation of these pyranoindolizine derivatives.

The above objects have now been achieved by the pyranoindolizine derivatives and their preparation processes as set forth in the appended claims.

The pyranoindolizine derivatives (I) of this invention can be easily converted to camptothecin and its derivatives, which have antitumor activities.

The above and other objects, features and advantages of the present invention will become apparent from the following description of the invention and the appended claims.

DETAILED DESCRIPTION OF THE PREFERRED EMBODIMENTS

In general, the compounds (I) of this invention can each be prepared, for example, in accordance with the following reaction scheme, by subjecting a compound (V) to a ring closing reaction to form a compound (Ia) of this invention, oxidizing the compound (Ia) to obtain a compound (Ib) of this invention and then subjecting the compound (Ib) to deketalizing reaction.

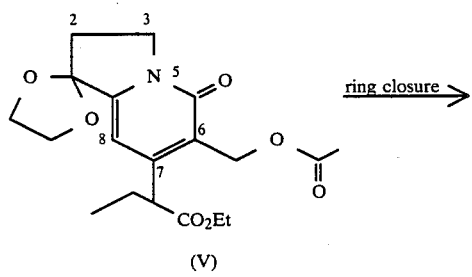

(V)

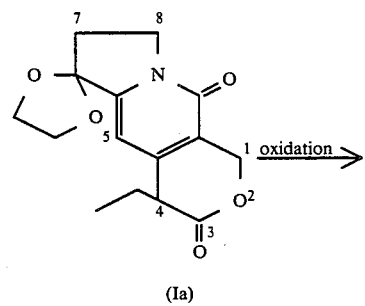

(Ia)

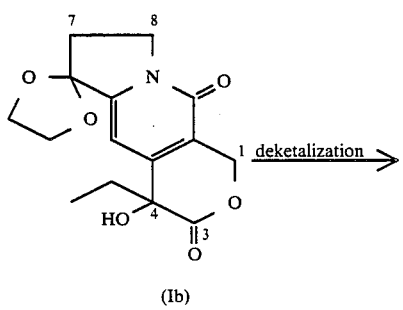

(Ib)

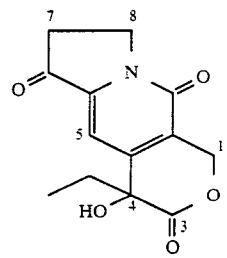

(Ic)

Namely, the compound (Ia) [in the formula (I), R=H and Q=

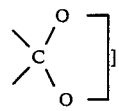

]

can be obtained by hydrolyzing ethyl 6-[(acetoxy)methyl]-α-ethyl-1,1-(ethylenedioxy)-5-oxo-1,2,3,5-tetrahydroindolizine-7-acetate (V) [M. C. Wani, et al., J. Med. Chem., 23, 554(1980)] in an alkaline solvent the pH of which has been adjusted with lithium hydroxide, sodium hydroxide, potassium hydroxide or the like, and then treating the resulting hydrolysate in an acidic solvent the pH of which has been adjusted with acetic acid, hydrochloric acid, sulfuric acid or the like. No particular limitation is imposed on these solvents so long as they are inert to their corresponding reactions. For example, alcohols such as methanol, dioxane, N,N-dimethylformamide, and the like may be used. The above compound (Ia) can be converted to the compound (Ib) having a hydroxyl group [in the formula (I), R=OH, Q=

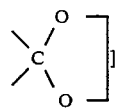

]

by dissolving the compound (Ia) in an inert solvent such as N,N-dimethylformamide and then introducing oxygen gas into the resultant solution in the presence of cupric acetate or cupric chloride, or an alkali metal alcoholate and a trialkyl phosphite or triaryl phosphite. Upon deketalization of the compound (Ib) in an acidic solvent which has been prepared using hydrochloric acid, sulfuric acid or the like, a compound (Ic) having a ketone group [in the formula (I), R=OH, Q=>C=O] can be obtained. Incidentally, 4-ethyl-7,8-dihydro-1H-pyrano[3,4-f]indolizine-3,6,10-(4H)-trione [in the formula (I), R=H, Q=>C=O], a known compound, can be derived when the compound (Ia) is subjected to deketalization in the same manner as described above except for the omission of introduction of the hydroxyl group.

On the other hand, the pyranoindolizine derivatives (I*) having the S-configuration may each be prepared, preferably, by the following exemplary processes.

Process 1

The pyranoindolizine derivative (I*) in which Q means >C=O [i.e., the compound (I*c)] can be prepared in accordance with the following reaction scheme, namely, by reacting the above-described compound (Ib) with (R)-(+)-α-methylbenzylamine or (S)-(−)-α-methylbenzylamine, isolating a compound represented by the formula (VI) or (VII) from the resulting mixture of diastereomers and then subjecting the compound (VI) or (VII) to an acid treatment.

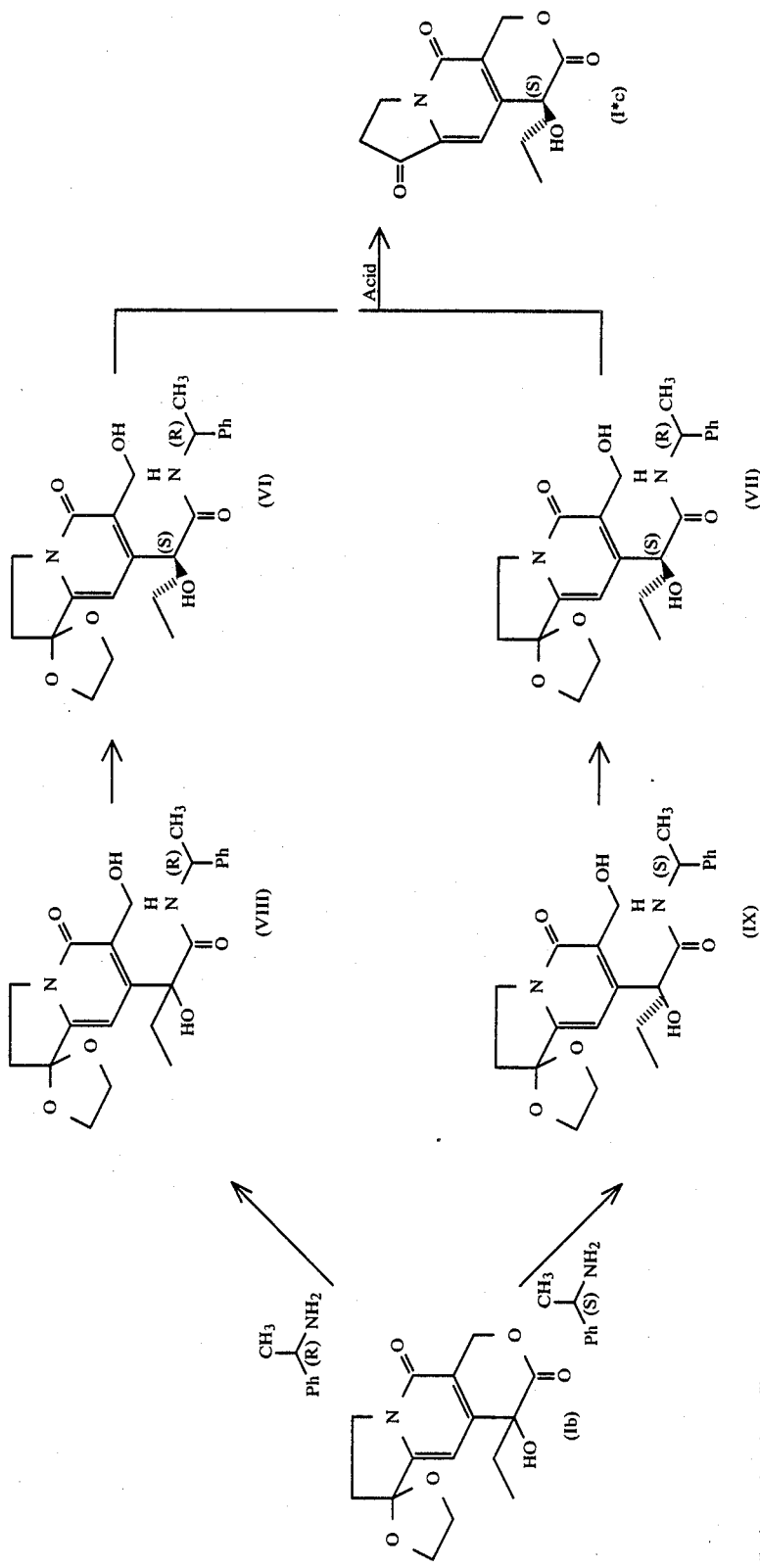

First of all, the compound (Ib) is reacted with (R)-(+)-α-methylbenzylamine or (S)-(−)-α-methylbenzylamine at a temperature of from about 20° C.–about 200° C. under a nitrogen gas stream to obtain the compound (VIII) or (IX) which is a mixture of two types of diastereomers. Upon subsequent separation of the mixture by a usual method such as fractional crystallization, the diastereomer (VI) or (VII) can be obtained. As illustrative solvents suitable for its crystallization and recrystallization, may be mentioned dichloromethane, n-hexane, benzene, isopropyl alcohol and the like. This separation of the diastereomers can be effected almost completely by 1–2 operations of recrystallization with a good recovery rate. Upon treatment of the thus-obtained diastereomer (VI) or (VII) in an acidic solvent which has been prepared using an acid such as hydrochloric acid, sulfuric acid or trifluoroacetic acid, the hydrolysis, lactonization and deketalization of the amide proceed parallelly so that the intended, optically-active compound (I*c) of this invention can be obtained.

Process 2

The pyranoindolizine derivative (I*) in which Q means

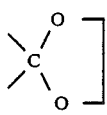

i.e., the compound (I*b)] can be derived from a compound represented by the formula (X) in accordance with the following reaction scheme.

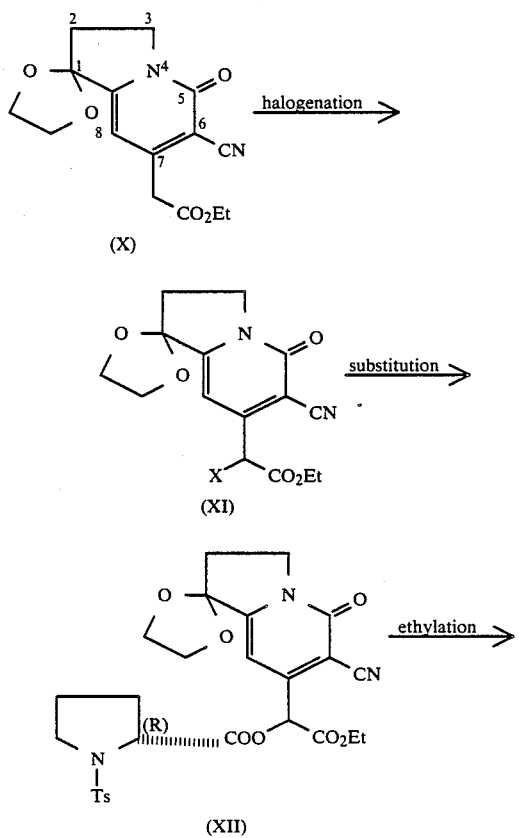

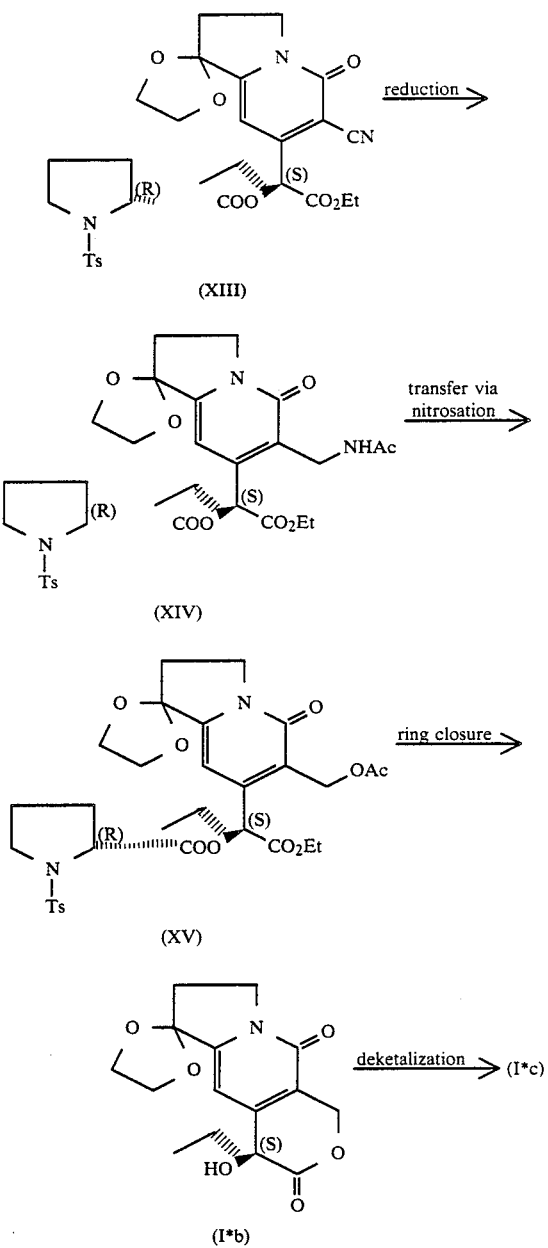

wherein X means a halogen atom and Ts denotes a tosyl group.

As shown by the above reaction scheme, this preparation process comprises a halogenating reaction, substituting reaction, ethylating reaction, reducing reaction, transfer reaction via nitrosation, and ring-closing reaction. These reactions will hereinafter be described respectively.

Halogenating reaction

The compound of the formula (XI) can be prepared by treating ethyl 6-cyano-1,1-(ethylenedioxy)-5-oxo-1,2,3,5-tetrahydroindolizine-7-acetate (X) [J. Med. Chem. 23, 554(1980)] together with a base such as sodium hydride or potassium t-butoxide in a solvent inert to the intended reaction such as 1,2-dimethoxyethane or N,N-dimethylformamide or a mixture of such solvents, followed by an addition of a halogen such as bromine or chlorine. The reaction is carried out generally at 0°–100° C. preferably, at 30°–80° C. and for 10 minutes–15 hours, preferably, for 20 minutes–5 hours.

Substituting reaction

The compound of the formula (XII) can be prepared by reacting the compound of the formula (XI) with an alkali metal salt such as the sodium or potassium salt of (R)-N-tosylproline in a solvent inert to the intended reaction such as N,N-dimethylformamide or N,N-dimethylacetamide. The reaction is carried out generally at 20°–100° C., preferably, at 50°–80° C. and for 5 minutes–5 hours, preferably, 10 minutes–1 hour.

Ethylating reaction

The compound of the formula (XIII) can be prepared by reacting the compound of the formula (XII) with a base such as sodium hydride or potassium t-butoxide in a solvent inert to the intended reaction such as N,N-dimethylformamide or 1,2-dimethoxyethane and then adding an ethylating agent such as ethyl iodide or diethyl sulfate. The reaction is carried out generally at −20°–50° C., preferably, 0°–30° C. and for 10 minutes–15 hours, preferably, 30 minutes–5 hours.

Reducing reaction

The compound of the formula (XIV) can be prepared by reacting the compound of the formula (XIII) in the presence of acetic anhydride and Raney nickel under a hydrogen gas stream, if necessary, while exposing the reaction mixture to light from a tungsten lamp. The reaction is carried out generally at 10°–100° C., preferably, at 20°–60° C. and for 10 minutes–8 hours, preferably, for 30 minutes–5 hours.

Transfer reaction via nitrosation

The compound of the formula (XV) can be prepared by reacting the compound of the formula (XIV) with a nitrosating agent such as sodium nitrite in a mixed solvent of acetic anhydride and acetic acid at 0°–50° C., preferably, at 0°–30° C. and for 30 minutes–15 hours, preferably, for 1 hour–5 hours and then heating with stirring the resultant nitroso derivative at 50°–120° C., preferably, at 60°–90° C. and for 30 minutes–12 hours, preferably, for 1 hour–5 hours.

Ring-closing reaction

The compound of the formula (I*b) can be prepared by hydrolyzing the compound of the formula (XV) with an aqueous solution of an alkali such as lithium hydroxide, sodium hydroxide or potassium hydroxide in a solvent inert to the intended reaction, e.g., an alcohol such as ethanol, dioxane or the like and then treating the hydrolysate in an acidic solvent the pH of which has been adjusted with acetic acid, citric acid or hydrochloric acid. The hydrolysis is effected at 0°–50° C., preferably, 20°–40° C. and for 5 minutes–5 hours, preferably, for 10 minutes–3 hours, while the reaction in the acidic solvent is carried out at 0°–70° C. preferably, at 10°–40° C. and for 1 hour–72 hours, preferably, for 12 hours–24 hours.

Deketalizing reaction

The compound (I*c) can be prepared from the compound (I*b) by treating the latter compound in the same manner as in the deketalizing reaction of the compound (Ib).

In accordance with the following exemplary reaction scheme, the above-obtained compounds (I) of this invention can each be converted to camptothecin (IV) having antitumor activities or the camptothecin derivative (II) described in Japanese Patent Laid-Open No. 39683/1983 referred to above and also having antitumor activities, for example, by condensing the compound (I) with N-(o-aminobenzylidene)-p-toluidine (XVI) or 2-amino-4-methoxypropiophenone (XVII); and further to the compound (III) by demethylating the camptothecin derivative (II).

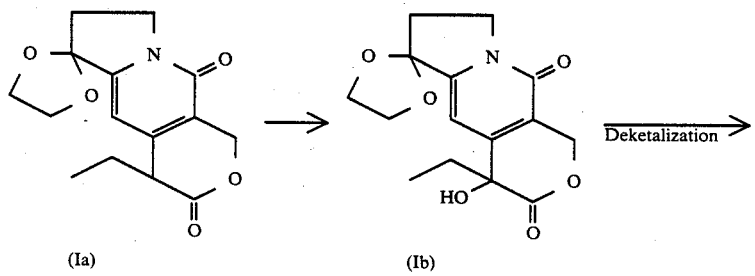

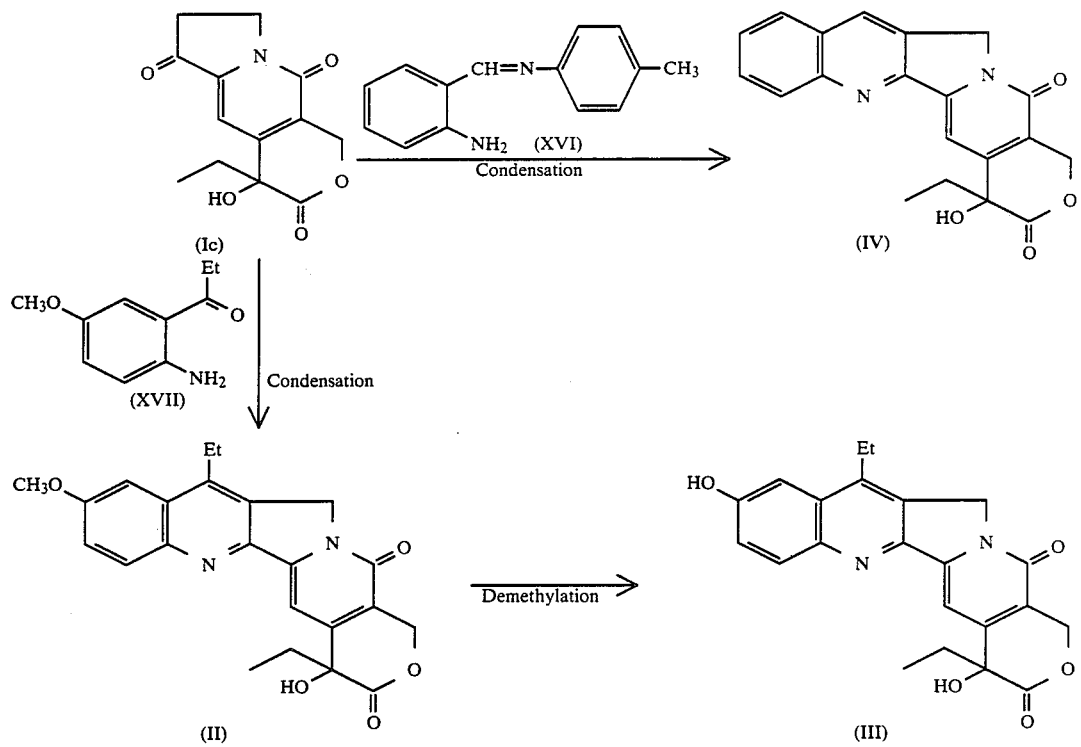

Namely, camptothecin (IV) or its derivative (II) can be derived by condensing the compound (Ic) of this invention, which has been obtained by treating the compound (Ib) of this invention in an acidic solvent prepared by using an acid such as trifluoroacetic acid, hydrochloric acid or sulfuric acid, with the compound of the formula (XVI) or (XVII) under conditions employed in a reaction called "Friedlaender synthesis". By demethylating the derivative (II) further, the compound (III) can also be obtained. The condensation can be carried out, for example, by heating the reaction mixture under reflux in the presence of p-toluenesulfonic acid or the like in an solvent inert to the reaction such as toluene or benzene by means of a Dean-Stark apparatus. On the other hand, the demethylating reaction can be effected, for example, by heating the derivative (II) under reflux in the presence of aluminum chloride or aluminum bromide in a solvent inert to the reaction such as toluene or benzene or by heating the derivative (II) under reflux in a solution of hydrobromic acid.

By the way, use of the pyranoindolizine derivatives of the formula (I*) as starting raw materials for the preparation of camptothecin and the like results in the provision of natural camptothecin (IV*) and natural camptothecin derivatives (II*) and (III*) represented respectively by the following formulae, leading to still better potential effects.

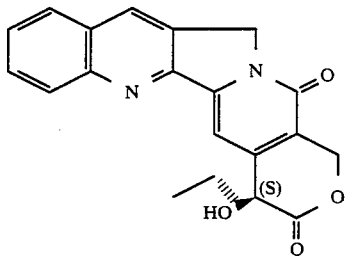

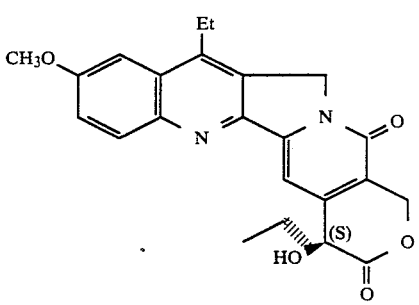

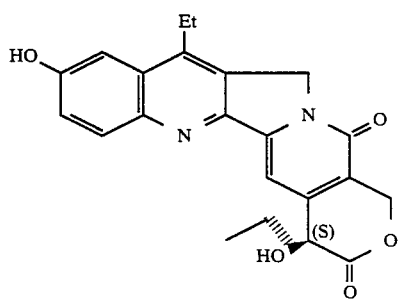

The present invention will hereinafter be described more specifically by the following Examples and Referential Examples.

Example 1

4-Ethyl-6,6-(ethylenedioxy)-7,8-dihydro-1H-pyrano[3,4-f]indolizine-3,10(4H)-dione (Ia)

Dissolved in 15 ml of methanol was 759 mg of ethyl 6-[(acetoxy)methyl]-α-ethyl-1,1-(ethylenedioxy)-5-oxo-1,2,3,5-tetrahydroindolizine-7-acetate (V), followed by an addition of 5 ml of water and a further addition of 420 mg of lithium hydroxide (monohydrate). The resultant mixture was stirred at room temperature for 2 hours. After removal of methanol by distillation, the residue was added first with about 10 ml of ice water and then with 1.5 ml of acetic acid, followed by stirring at room temperature for 22 hours.

The reaction mixture was extracted with dichloromethane and after washing the extract with water, the dichloromethane solution was dried over anhydrous sodium sulfate. The solvent was then distilled off and upon recrystallization of the residue from a mixed solvent of dichloromethane and n-hexane, 535 mg of the title compound was obtained as colorless crystals.

Melting point: 130°–131° C.

NMR (CDCl$_3$) δ: 1.01(3H, t, J=7 Hz, CH$_3$—), 1.95(2H, m, —CH$_2$CH$_3$), 2.37(2H, t, J=7 Hz, C$_7$13 H), 3.43(1H, t, J=6 Hz, C$_4$—H), 4.12(6H, m, —O—CH$_2$CH$_2$—O— and C$_8$—H), 5.27(2H, ABq, J=17 Hz, C$_1$—H), 6.11(1H, s, C$_5$—H).

IR $\nu_{max}^{KBr}$ cm$^{-1}$: 1732, 1608.

Elemental analysis: Calculated for C$_{15}$H$_{17}$NO$_5$: C, 61.85; H, 5.88; N, 4.81. Found: C, 61.71; H, 5.85; N, 4.79.

EXAMPLE 2

4-Ethyl-6,6-(ethylenedioxy)-7,8-dihydro-4-hydroxy-1H-pyrano[3,4-f]indolizine-3,10(4H)-dione (Ib)

Dissolved in 15 ml of N,N-dimethylformamide were 300 mg of the compound (Ia) obtained in Example 1, 352 mg of cupric acetate and 50 μl of 50% dimethylamine. The reaction mixture was then stirred at room temperature for 1 hour while introducing oxygen gas. After removal of the solvent by distillation, the residue was dissolved in dichloromethane and the resulting dichloromethane solution was washed with water. The organic layer was dried over anhydrous sodium sulfate and the solvent was then distilled off. The residue was thereafter subjected to column chromatography on silica gel (7 g) as a carrier. A yellowish oily substance which had been obtained from a 1:1 eluate of benzene and ethyl acetate was recrystallized from a mixed solvent of dichloromethane and n-hexane, thereby obtaining 135 mg of the title compound as colorless needle-like crystals.

Melting point: 180°–181° C.

NMR (CDCl$_3$) δ: 0.96(3H, t, J=7 Hz, CH$_3$—), 1.77(2H, q, J=7 Hz, CH$_3$CH$_2$—), 2.38(2H, t, J=7 Hz, C$_7$—H), 4.12(6H, m, —O—CH$_2$CH$_2$—O— and C$_8$—H), 5.30(2H, ABq, J=16 Hz, C$_1$—H), 6.53(1H, s, C$_5$—H).

IR $\nu_{max}^{KBr}$ cm$^{-1}$: 3250, 1745, 1650.

Elemental analysis: Calculated for C$_{15}$H$_{17}$NO$_6$: C, 58.63; H, 5.58; N, 4.56. Found: C, 58.56; H, 5.57; N, 4.56.

EXAMPLE 3

4-Ethyl-6,6-(ethylenedioxy)-7,8-dihydro-4-hydroxy-1H-pyrano[3,4-f]indolizine-3,10(4H)-dione (Ib)

Dissolved in 200 ml of N,N-dimethylformamide was 9.96 g of the compound (Ia) obtained in Example 1, followed by an addition of 5.01 g of potassium tert-butoxide at −40° C. The resulting mixture was stirred for 20 minutes. Twenty-one milliliters of triethyl phosphite were added and the reaction mixture was then stirred for 2 hours and 30 minutes while introducing oxygen gas. Thereafter, 6 ml of concentrated hydrochloric acid was added to lower the pH to 1. After stirring the reaction mixture for 20 minutes, 2.5 ml of concentrated aqueous ammonia was added to adjust the pH to 8. The solvent was distilled off, and the residue was dissolved in dichloromethane and the thus-prepared dichloromethane solution was then washed with water. After drying the organic layer over anhydrous sodium sulfate, the solvent was distilled off and n-hexane was added to the residue, followed by stirring of the resulting mixture. Insoluble matter was collected by filtration and then recrystallized from a mixed solvent of dichloromethane and n-hexane, thereby obtaining 8.10 g of the title compound as colorless needle-like crystals.

The melting point, NMR data and IR data of the above-obtained compound were consistent with those of the compound obtained in Example 2.

EXAMPLE 4

4-Ethyl-7,8-dihydro-4-hydroxy-1H-pyrano[3,4-f]indolizine-3,6,10(4H)-trione (Ic)

Dissolved in 15 ml of acetone was 500 mg of the compound (Ib) obtained in Example 2, followed by an addition of 1 ml of 2N sulfuric acid. The resulting mixture was stirred for 5 hours at room temperature. After removal of acetone by distillation, the residue was dissolved in dichloromethane and the resulting dichloromethane solution was washed with water. After drying the organic layer over anhydrous sodium sulfate, the solvent was distilled off. Upon recrystallization of the residue from ethyl ether, 260 mg of the title compound was obtained as pale yellowish granular crystals.

Melting point: 193°–195° C. (decomposed).

NMR (CDCl$_3$) δ: 0.96(3H, t, J=7 Hz, CH$_3$—), 1.80(2H, q, J=7 Hz, CH$_3$CH$_2$—), 2.93(2H, t, J=7 Hz, C$_7$—H), 4.30(2H, t, J=7 Hz, C$_8$—H), 5.37(2H, ABq, J=17 Hz, C$_1$—H), 7.16(1H, s, C$_5$—H).

IR $\nu_{max}^{KBr}$ cm$^{-1}$: 1740, 1660.

Elemental analysis: Calculated for C$_{13}$H$_{13}$NO$_5$: C, 59.31; H, 4.98; N, 5.32. Found: C, 59.19; H, 5.15; N, 5.19.

EXAMPLE 5

(1)

(S)-α-Ethyl-1,1-(ethylenedioxy)-α-hydroxy-6-(hydroxymethyl)-N-[(R)-1-phenylethyl]-5-oxo-1,2,3,5-tetrahydroindolizine-7-acetamide (VI)

Three grams of the compound (Ib) obtained in Example 2 were added to 5.9 g of R-(+)-α-methylbenzylamine and the resultant mixture was stirred at 80° C. for 20 hours under a nitrogen gas stream. After completion of the reaction, 200 ml of dichloromethane was added and the resultant mixture was washed first with 10% citric acid and then with water. After drying the mixture over anhydrous sodium sulfate, the solvent was distilled off. The residue was purified by column chromatography on silica gel (100 g). A colorless oily substance was obtained from a 98:2 eluate of chloroform and methanol. The oily substance was then recrystallized from a mixed solvent of dichloromethane and n-hexane so as to crystalize same, thereby obtaining 2.7 g of colorless crystals. The crystals were then dissolved in hot benzene and the resultant benzene solution was allowed to stand overnight. The resulting precipitate was filtered off and the filtrate was concentrated to dryness to obtain 1.35 g of a colorless foam. The foam was then crystallized from a mixed solvent of dichloromethane and n-hexane. Recrystallization was further repeated twice from a mixed solvent of dichloromethane and n-hexane, thereby obtaining 1.25 g of the title compound as colorless flaky crystals.

Melting point: 119°–120° C.

NMR (CDCl$_3$) δ: 0.99(3H, t, J=7 Hz, CH$_3$CH$_2$—), 1.52(3H, d, J=7 Hz, CH$_3$CH—, 2.30(2H, t, J=7 Hz, C$_2$—H), 4.04(6H, m, —O—(CH$_2$)$_2$—O—, C$_3$—H), 4.68(2H, ABq, J=12.5 Hz, CH$_2$OH), 5.07(1H, m, CHCH$_3$), 6.60(1H, s, C$_8$—H). 7.29(5H, s, Ph).

IR $\nu_{max}^{KBr}$ cm$^{-1}$: 3400, 1650, 1585.

Elemental analysis: Calculated for C$_{23}$H$_{28}$N$_2$O$_4$·$\frac{3}{4}$H$_2$O: C, 62.50; H, 6.73; N, 6.34. Found: C, 62.49; H, 6.45; N, 6.25.

(2)
(S)-4-Ethyl-7,8-dihydro-4-hydroxy-1H-pyrano-[3,4-f]indolizine-3,6,10(4H)-trione (I*c)

Dissolved in 15 ml of dimethoxyethane was 815 mg of the compound (VI) obtained in the above procedure (1), followed by an addition of 5 ml of 2N H$_2$SO$_4$. The thus-prepared solution was heated with stirring for 20 hours under a nitrogen gas stream. After completion of the reaction, 150 ml of dichloromethane was added and the resultant mixture was washed with water. The organic layer was then dried over anhydrous sodium sulfate and the solvent was distilled off. The residue was recrystallized from a mixed solvent of ethanol and petroleum ether to obtain 315 mg of the title compound as colorless needle-like crystals.

Melting point: 176°–177° C. (decomposed).

Specific rotatory power [α]$_D$= +120.57° (C=0.622, chloroform).

NMR (CDCl$_3$) δ: 0.98(3H, t, J=7 Hz, CH$_3$CH$_2$—), 1.82(2H, q, J=7 Hz, CH$_3$CH$_2$—), 2.96(2H, t, J=7 Hz, C$_7$—H), 3.71(1H, s, OH), 4.35(2H, t, J=7 Hz, C$_8$—H), 5.46(2H, ABq, J=17 Hz, C$_1$—H), 7.23(1H, s, C$_5$—H).

IR $\nu_{max}^{KBr}$ cm$^{-1}$: 3430, 1740, 1660, 1610, 1155.

Elemental analysis: Calculated for C$_{13}$H$_{13}$NO$_5$: C, 59.31; H, 4.98; N, 5.32. Found: C, 59.18; H, 5.03; N, 5.28.

EXAMPLE 6

(1)
(S)-α-Ethyl-1,1-(ethylenedioxy)-α-hydroxy-6-(hydroxymethyl)-N-[(S)-1-phenylethyl]-5-oxo-1,2,3,5-tetrahydroindolizine-7-acetamide (VII)

Added to 3 ml of S-(—)-α-methylbenzylamine was 1 g of the compound (Ib) obtained in Example 2 and the resulting mixture was stirred at 100° C. for 18 hours under a nitrogen gas stream. After completion of the reaction, 150 ml of dichloromethane was added and the resulting mixture was washed first with 10% citric acid and then with water. The mixture was then dried over anhydrous sodium sulfate and the solvent was thereafter distilled off. The residue was purified by column chromatography on silica gel (30 g). From a 98:2 eluate of chloroform and methanol, 1 g of a colorless oily substance was obtained. The oily substance was recrystallized from a mixed solvent of dichloromethane and n-hexane. Then, 900 mg of colorless crystals were obtained by filtration. The thus-obtained crystals were dissolved in hot benzene and the resultant benzene solution was allowed to stand overnight. Precipitated crystals were collected by filtration to obtain 460 mg of colorless needle-like crystals. The crystals were recrystallized again from a mixed solvent of dichloromethane and n-hexane, thereby obtaining 380 mg of the title compound as colorless needle-like crystals.

Melting point: 115°–116° C.

NMR (CDCl$_3$) δ: 0.88(3H, t, J=7 Hz, CH$_3$CH$_2$—), 1.50(3H, d, J=7 Hz, CH$_3$CH—), 2.32(2H, t, J=7 Hz, C$_2$—H), 4.10(6H, m, —O—(CH$_2$)$_2$—O, C$_3$—H), 4.88(2H, ABq, J=12.6 Hz, CH$_2$OH), 5.10(1H, m, CHCH$_3$), 6.67(1H, s, C$_8$—H) 7.32(5H, s, Ph).

IR $\nu_{max}^{KBr}$ cm$^{-1}$: 3400, 1740, 1650, 1585.

Elemental analysis: Calculated for C$_{23}$H$_{28}$N$_2$O$_4$·$\frac{1}{4}$H$_2$O: C, 63.80; H, 6.63; N, 6.47. Found: C, 63.51; H, 6.69; N, 6.45.

(2)
(S)-4-Ethyl-7,8-dihydro-4-hydroxy-1H-pyrano-[3,4-f]indolizine-3,6,10(4H)-trione (I*c)

Three hundred milligrams of the compound (VII) obtained in the above procedure (1) were dissolved in 80% trifluoroacetic acid solution and the resulting mixture was stirred at room temperature for 2 hours under a nitrogen gas stream. The reaction mixture was concentrated to dryness and the residue was purified by column chromatography on silica gel (10 g). A colorless oily substance was obtained from a 98:2 eluate of chloroform and methanol. The oily substance was crystallized from a mixed solvent of ethanol and petroleum ether to obtain 170 mg of the title compound as colorless needle-like crystals.

Specific rotatory power [α]$_D$= +121.42° (C=0.532, chloroform).

The melting point, NMR data and IR data of the above-obtained crystals were in full conformity with those of the compound obtained in the procedure (2) of Example 5.

EXAMPLE 7

(1) Ethyl α-bromo-6-cyano-1,1-(ethylenedioxy)-5-oxo-1,2,3,5-tetrahydroindolizine-7-acetate (XI)

Dissolved in 60 ml of 1,2-dimethoxyethane was 3.04 g of the compound (X), followed by an addition of 440 mg of 60% NaH. After stirring the resultant mixture at 80° C. for 10 minutes, the reaction mixture was cooled down to room temperature, at which 0.77 ml of bromine was added. The reaction mixture was then stirred for 2 hours. The reaction mixture was concentrated under reduced pressure and the residue was dissolved in chloroform. The chloroform solution was successively washed with 10% citric acid, 10% Na$_2$S$_2$O$_3$ and water in order. After drying the thus-washed chloroform solution over anhydrous sodium sulfate, the chloroform solution was concentrated. The residue was solidified from a mixed solvent of chloroform and ethyl ether and the resulting solid matter was collected by filtration to obtain 3.72 g of the title compound.

Melting point: 161°–163° C. (decomposed).

NMR (CDCl₃) δ: 1.32(3H, t, J=7 Hz, —CH₂CH₃), 2.42(2H, t, J=7 Hz, C₂—H), 4.16(4H, s, —O—(CH₂)₂—O—), 4.0-4.5(4H, m, C₃—H, —CH₂CH₃), 5.55(1H, s, —CHBr—), 6.60(1H, s, C₈—H)

IR ν_max^KBr cm⁻¹: 2230, 1745, 1650.

Elemental analysis: Calculated for C₁₅H₁₅N₂O₅Br: C, 47.02; H, 3.95; N, 7.31. Found: C, 46.97; H, 3.87; N, 7.34.

(2) Ethyl 2-cyano-1,1-(ethylenedioxy)-α-[(R)-1-(p-toluenesulfonyl)pyrrolidin-2-ylcarbonyloxy]-5-oxo-1,2,3,5-tetrahydroindolizine-7-acetate (XII)

Dissolved in 50 ml of N,N-dimethylformamide was 14.37 g of (R)-N-tosylproline, followed by an addition of 1.91 g of anhydrous Na₂CO₃. Under a nitrogen gas stream, 9.35 g of the compound (XI) obtained in the above procedure (1) was added and the resultant mixture was stirred at 70° C. for 1 hour. After concentrating the reaction mixture under reduced pressure, the residue was dissolved in chloroform. The chloroform solution was washed successively with water, 5% NaHCO₃ and water and was then dried over anhydrous magnesium sulfate. The thus-dried chloroform solution was then concentrated. The residue was treated by column chromatography on silica gel and then developed with a 2:1 mixed solvent of toluene and ethyl acetate. A fraction containing the intended compound was concentrated to dryness, thereby obtaining 13.0 g of the title compound.

NMR (CDCl₃) δ: 1.28,1.30(each 1.5H, each t, each J=7 Hz, 13 CH₂CH₃), 1.5-2.6(6H, m, C₂—H, —CH₂—CH₂—), 2.43(3H, s, —CH₃), 3.0-3.8(2H, m, —CH₂—), 3.8-4.6(9H, m, —O—(CH₂)₂—O—, —CH₂CH₃, C₃—H,

6.18,6.29(each 0.5H, each s), 6.61,6.64(each 0.5H, each s, C₈—H), 7.31(2H, d, J=9 Hz, Ph), 7.72(2H, d, J=9 Hz, Ph).

IR ν_max^KBr cm⁻¹: 2224, 1764, 1664.

Elemental analysis: Calculated for C₂₇H₂₉N₃O₉S.¾H₂O: C, 55.42; H, 5.25; N, 7.18. Found: C, 55.44; H, 4.99; N, 7.30.

(3) Ethyl (S)-6-cyano-α-ethyl-1,1-(ethylenedioxy)-α-[(R)-1-(p-toluenesulfonyl)pyrrolidin-2-ylcarbonyloxy]-5-oxo-1,2,3,5-tetrahydroindolizine-7-acetate (XIII)

Dissolved in 28 ml of anhydrous N,N-dimethylformamide was 3.50 g of the compound (XII) obtained in the above procedure (2), followed by an addition of 248 mg of 60% NaH. After stirring the resultant mixture at room temperature for 1 hour, 5 ml of ethyl iodide was added and the resulting mixture was stirred at room temperature for 3 hours. After concentration of the reaction mixture under reduced pressure, the residue was dissolved in chloroform and the resulting chloroform solution was washed first with a 10% citric acid solution and then with water. The chloroform solution was dried over anhydrous sodium sulfate and then concentrated. The residue was subjected to column chromatography on silica gel and then developed with a 3:1 mixed solvent of benzene and ethyl acetate. A fraction containing the intended product was concentrated. The residue was crystallized from 2-propanol to obtain 2.07 g of the title compound.

Melting pint: 75°-80° C.

NMR (CDCl₃) δ: 0.90(3H, t, J=7 Hz, —CH₂CH₃), 1.31(3H, t, J=7 Hz, 13 CH₂CH₃), 1.5-2.5(4H, m, —(CH₂)₂—), 2.43(3H, s, —CH₃), 2.1-2.8(4H, m, C₂—H, —CH₂CH₃), 3.0-3.8(2H, m, —CH₂—), 3.8-4.6(9H, m, —O—(CH₂)₂—O—,

—CH₂×2), 6.61(1H, s, C₈—H), 7.32(2H, d, J=8 Hz, Ph), 7.18(2H, d, J=8 Hz, Ph).

IR ν_max^KBr cm⁻¹: 1764, 1662.

Elemental analysis: Calculated for C₂₉H₃₃N₃O₉S: C, 58.09; H, 5.55; N, 7.01. Found: C, 57.98; H, 5.67; N, 7.02.

(4) Ethyl (S)-6-(acetylaminomethyl)-α-ethyl-1,1-(ethylenedioxy)-α-[(R)-1-(p-toluenesulfonyl)pyrrolidin-2-ylcarbonyloxy]-5-oxo-1,2,3,5-tetrahydroindolizine-7-acetate (XIV)

To a mixed solvent which was composed of 20 ml of acetic acid and 50 ml of acetic anhydride and containing 6 g of Raney nickel, 2.00 g of the compound (XIII) obtained in the above procedure (3) was added. While exposing the reaction system to light from a tungsten lamp, the compound (XIII) was reduced for 2 hours under a hydrogen gas stream. After removal of Raney nickel by filtration, the filtrate was concentrated. The residue was subjected to column chromatography on silica gel and then developed by a 50:1 mixed solvent of chloroform and methanol. A fraction containing the intended product was concentrated to dryness, thereby obtaining 2.15 g of the title compound in an amorphous form.

NMR (CDCl₃) δ:0.89 (3H, t, J=7 Hz, —CH₂CH₃), 1.29(3H, t, J=7 Hz, —CH₂CH₃), 1.95(3H, s, —COCH₃), 2.24(3H, s, —CH₃), 1.5-2.8(8H, m, C₂—H, —(CH₂)₂—, —CH₂CH₃), 3.0-3.8(2H, m, —CH₂—), 3.8-5.0(11H, m, —O—(CH₂)₂—O—, —CH₂CH₃, —CH₂NH—, C₃—H,

6.78 (1H, S, C₈—H), 7.0-7.5(1H, br.s, —NH—), 7.39(2H, d, J=7 Hz, Ph), 7.84(2H, d, J=7 Hz, Ph).

IR ν_max^KBr cm⁻¹: 1745, 1645, 1590.

Elemental analysis: Calculated for C₃₁H₃₉N₃O₁₀S.1¼H₂O: C, 55.72; H, 6.26; N, 6.29. Found: C, 55.59; H, 5.75; N, 6.39.

(5) Ethyl (S)-6-(acetoxymethyl)-α-ethyl-1,1-(ethylenedioxy)-α-[(R)-1-(p-toluenesulfoyl)-pyrrolidin-2-ylcarbonyloxy]-5-oxo-1,2,3,5-tetrahydroindolizine-7-acetate (XV)

In a mixed solvent composed of 26 ml of acetic anhydride and 8 ml of acetic acid, 1.98 g of the compound (XIV) obtained in the above procedure (4) was dissolved, followed by an addition of 1.1 g of NaNo₂ with ice-cooling. The resultant solution was stirred for 5 hours at the same temperature. After concentration of the reaction mixture under reduced pressure, 120 ml of carbon tetrachloride was added to the residue and the resultant mixture was then heated under reflux for 5 hours. After allowing the reaction mixture to cool down, it was washed successively with water, 5% NaHCO₃ and water, and was then dried over anhydrous sodium sulfate and concentrated. The residue was subjected to column chromatography on silica gel and then developed by a 70:1 mixed solvent of chloroform and methanol. A fraction containing the intended product was concentrated to dryness, thereby obtaining 1.46 g of the title compound in an amorphous form.

NMR (CDCl$_3$) δ: 0.89(3H, t, J=7 Hz, —CH$_2$CH$_3$), 1.23(3H, t, J=7 Hz, —CH$_2$CH$_3$), 2.04(3H, s, —COCH$_3$), 1.5–2.8(8H, m, C$_2$—H, —CH$_2$CH$_3$, —(CH$_2$)$_2$—), 2.43(3H, s, —CH$_3$), 3.0–4.0(2H, m, —CH$_2$—), 3.9–4.6(9H, m, C$_3$—H, —CH$_2$CH$_3$, —O—(CH$_2$)$_2$—O—,

|
—CH—), 5.24(2H, s, —CH$_2$O—), 6.76(1H, s, C$_8$—H), 7.29(2H, d, J=8 Hz, Ph), 7.75(2H, d, J=8 Hz, Ph).

IR $\nu_{max}^{KBr}$ cm$^{-1}$: 1746, 1659, 1614.

Elemental analysis: Calculated for C$_{31}$H$_{38}$N$_2$O$_{11}$S.½H$_2$O: C, 56.78; H, 5.99; N, 4.27. Found: C, 56.60; H, 5.82; N, 4.19.

(6)
(S)-4-Ethyl-6,6-(ethylenedioxy)-7,8-dihydro-4-hydroxy-1H-pyrano[3,4-f]indolizine-3,10(4H)-dione (I*b)

In a mixed solvent composed of 6 ml of ethanol and 3 ml of water, 324 mg of the compound (XV) obtained in the above procedure (5) was dissolved, followed by an addition of 72 mg of lithium hydroxide monohydrate with ice-cooling. The resultant mixture was then stirred for 1 hour. After removal of ethanol by distillation, a small amount of water, 2 ml of acetic acid and 1 ml of dichloromethane were added successively. The thus-obtained mixture was then stirred at room temperature for 20 hours. The reaction mixture was extracted with dichloromethane and the extract was then washed with water, 5% NaHCO$_3$ and water successively. It was dried over anhydrous sodium sulfate and concentrated. The residue was subjected to column chromatography on silica gel and then developed by a 50:1 mixed solvent of chloroform and methanol. A fraction containing the intended product was concentrated to dryness. The thus-obtained oily substance was recrystallized from a mixed solvent of dichloromethane and n-hexane, thereby obtaining 1.38 g of the title compound as needle-like crystals.

Melting point: 170°–171° C.

Specific rotatory power [α]$_D$+109.7° (C=0.76, CHCl$_3$).

NMR (CDCl$_3$) δ: 0.97(3H, t, J=7 Hz, 13 CH$_2$CH$_3$), 1.80(2H, q, J=7 Hz, —CH$_2$CH$_3$), 2.42(2H, dd, J=7 Hz, 6 Hz, —CH$_2$—), 3.6–4.5(6H, m, —O—(CH$_2$)$_2$—O—, —CH$_2$), 5.17,5.57(2H, ABq, J=16 Hz, —CH$_2$—), 6.58(1H, s, C$_5$—H),

IR $\nu_{max}^{KBr}$ cm$^{-1}$: 1745, 1650.

Elemental analysis: Calculated for C$_{15}$H$_{17}$NO$_6$.½H$_2$O: C, 56.96; H, 5.74; N, 4.43. Found: C, 56.82; H, 5.53; N, 4.53.

EXAMPLE 8
(S)-7,8-Dihydro-4-ethyl-4-hydroxy-1H-pyrano[3,4-f]indolizine-3,6,10(4H)-trione (I*c)

Dissolved in 80% trifluoroacetic acid was 120 mg of the compound (I*b) of this invention obtained in the procedure (6) of Example 7. The resultant mixture was continuously stirred at room temperature for 1.5 hours under a nitrogen gas stream. The reaction mixture was concentrated and dichloromethane was added to the residue. After washing the thus-prepared mixture first with 5% NaHCO$_3$ and then with water, the mixture was dried over anhydrous sodium sulfate and then concentrated. The residue was crystallized from a mixed solvent of ethanol and petroleum ether to obtain 81 mg of the title compound as colorless needle-like crystals.

Melting point: 172°–174° C.

Specific rotatory power [α]$_D$+117.6° (C=0.56, chloroform).

NMR (CDCl$_3$) δ: 0.98(3H, t, J=7 Hz, —CH$_2$CH$_3$), 1.82(2H, q, J=7 Hz, —CH$_2$CH$_3$), 2.96(2H, t, J=7 Hz, C$_7$—H), 3.75(1H, s, —OH), 4.35(2H, t, J=7 Hz, C$_8$—H) 5.24,5.63(2H, ABq, J=17 Hz, C$_1$—H), 7.23(1H, s, C$_5$—H),

IR $\nu_{max}^{KBr}$ cm$^{-1}$: 1740, 1660, 1610.

Elemental analysis: Calculated for C$_{13}$H$_{13}$NO$_5$.½H$_2$O: C, 58.32; H, 5.08; N, 5.23. Found: C, 58.15; H, 4.89; N, 5.27.

REFERENTIAL EXAMPLE 1
7-Ethyl-10-methoxycamptothecin (II)

Dissolved in 25 ml of toluene were 200 mg of the compound (Ic) obtained in Example 4, 150 mg of 2-amino-5-methoxypropiophenone and 5 mg of p-toluenesulfonic acid. The resulting solution was heated under reflux for about 4.5 hours by means of a Dean-Stark apparatus. After allowing the reaction mixture to cool down, the resultant precipitate was collected by filtration, washed with acetone and then recrystallized from a mixed solvent of chloroform and methanol, thereby obtaining 290 mg of the title compound as pale yellowish crystals.

Melting point: 265°–269° C.

NMR (DMSO-d$_6$) δ: 0.88(3H, t, J=7 Hz, CH$_3$CH$_2$—C$_{20}$), 1.34(3H, t, J=7 Hz, CH$_3$CH$_2$—C$_7$), 3.97(3H, s, CH$_3$O), 5.30(2H, s, C$_5$—H or C$_{17}$—H), 5.42(2H, s, C$_{17}$—H or C$_5$—H), 6.45(1H, s, OH), 7.26(1H, s, C$_{14}$—H), 7.50(2H, m, C$_9$—H and C$_{11}$—H), 8.09(1H, d, J=8 Hz, C$_{12}$—H).

IR $\nu_{max}^{KBr}$ cm$^{-1}$: 1740, 1650.

Elemental analsis: Calculated for C$_{23}$H$_{22}$N$_2$O$_5$.½H$_2$O: C, 66.50; H, 5.58; N, 6.74. Found C, 66.70; H, 5.41; N, 6.79.

REFERENTIAL EXAMPLE 2
7-Ethyl-10-hydroxycamptothecin (III)

Dissolved in 80 ml of toluene was 400 mg of the compound (II) obtained in Referential Example 1, followed by an addition of 500 mg of aluminum chloride. The resultant mixture was heated under reflux for 6 hours. After allowing the reaction mixture to cool down, ice water was added, and the resulting precipitate was collected by filtration and then washed with water. Upon their recrystallization from ethanol, 280 mg of the title compound was obtained as pale yellowish crystals.

Melting point: 268°–271° C. (decomposed).

NMR (DMSO-d$_6$) δ: 0.89(3H, t, J=7 Hz, CH$_3$CH$_2$—C$_{20}$), 1.32(3H, t, J=7 Hz, CH$_3$CH$_2$—C$_7$), 1.88 (2H, q, J=7 Hz, CH$_3$CH$_2$—C$_{20}$), 5.27(2H, s, C$_5$—H or C$_{17}$—H), 5.41(2H, s, C$_5$—H or C$_{17}$—H), 6.44(1H, br.s, OH), 7.27(1H, s, C$_{14}$—H), 7.42(2H, m, C$_9$—H and C$_{11}$—H), 8.01(1H, d, J=10 Hz, C$_{12}$—H).

IR $\nu_{max}^{KBr}$ cm$^{-1}$: 1740, 1654.

Elemental analysis: Calculated for $C_{22}H_{20}N_2O_5 \cdot 2H_2O$: C, 61.68; H, 5.65; N, 6.54. Found: C, 61.58; H, 5.36; N, 6.19.

REFERENTIAL EXAMPLE 3

(20S)-(+)-Camptothecin (IV*)

A reaction mixture, which had been obtained by adding 450 mg of the compound (I*c) obtained in Example 8 and 430 mg of N-(o-aminobenzylidene)-p-toluidine (XVI) to 100 ml of toluene, was heated with stirring for 30 minutes by means of a Dean-Stark apparatus. Five milligrams of p-toluenesulfonic acid were then added and the resulting mixture was heated with stirring for additional 2.5 hours. After allowing the reaction mixture to cool down, precipitated crystals were collected by filtration. After washing them with acetone, they were dried to obtain 500 mg of the title compound as yellowish crystalline powder.

Melting point: 265°–266° C. (decomposed).

Specific rotatory power $[\alpha]_D + 41.96°$ (C=0.51, chloroform:methanol=8:2).

NMR (DMSO-d$_6$) δ: 0.90(3H, t, J=7.5 Hz, $CH_3CH_2$—), 1.89(2H, q, J=7.5 Hz, $CH_3CH_2$—), 5.32(2H, s, $CH_2N$ or $CH_2O$), 5.45(2H, s, $CH_2O$ or $CH_2N$), 6.54(1H, s, OH), 7.40(1H, s, $C_4$—H), 7.60–8.30(4H, m, Ar.), 8.74(1H, s, $C_7$—H).

IR $\nu_{max}^{KBr}$ cm$^{-1}$: 3440, 1750, 1660, 1610, 1585.

Elemental analysis: Calculated for $C_{20}H_{16}N_2O_4$: C, 68.96; H, 4.63; N, 8.04. Found: C, 68.81; H, 4.85; N, 7.95.

REFERENTIAL EXAMPLE 4

(20S)-7-Ethyl-10-methoxycamptothecin (II*)

A reaction mixture, which had been obtained by adding 1 g of the compound (I*c) obtained in Example 8 and 750 mg of 2-amino-5-methoxypropiophenone (XVII) to 150 ml of toluene, was heated with stirring for 1 hour by means of a Dean-Stark apparatus. Ten milligrams of p-toluenesulfonic acid were then added and the resulting mixture was heated with stirring for additional 2.5 hours. After allowing the reaction mixture to cool down, precipitated crystals were collected by filtration. After washing them thoroughly with acetone, they were dried to obtain 1.45 g of the title compound as yellowish white needle-like crystals.

Melting point: 258°–261° C. (decomposed).

Specific rotatory power $[\alpha]_D + 39.50°$ (C=0.324, chloroform:methanol=8:2).

NMR (DMSO-d$_6$) δ: 0.83(3H, t, J=7 Hz, $CH_3CH_2$—), 1.28(3H, t, J=7 Hz, $CH_3CH_2$—), 1.82(2H, q, J=7 Hz, $CH_3CH_2$—), 3.93(3H, s, $CH_3O$), 5.24(2H, s, $CH_2N$ or $CH_2O$), 5.36(2H, s, $CH_2O$ or $CH_2N$), 6.39(1H, s, OH), 7.23(1H, s, $C_4$—H), 7.36–7.60(2H, m, $C_{11}$—H, $C_{12}$—H), 8.01(1H, d, J=10 Hz, $C_9$—H).

Elemental analysis: Calculated for $C_{23}H_{22}N_2O_5$: C, 67.96; H, 5.46; N, 6.89. Found: C, 67.82; H, 5.35; N, 6.84.

REFERENTIAL EXAMPLE 5

(20S)-7-Ethyl-10-hydroxycamptothecin (III*)

Five hundred milligrams of the compound (II*) obtained in Referential Example 4 were added to 10 ml of a 47% HBr solution and the resultant mixture was heated under reflux for 2.5 hours under a nitrogen gas stream. After completion of the reaction, the reaction mixture was concentrated to dryness and the residue was added with acetone, thereby converting the residue into powder. The thus-formed yellowish powder was collected by filtration. It was then recrystallized from a mixed solvent of methanol and chloroform to obtain 430 mg of yellowish white, needle-like crystals.

Melting point: 232°–235° C. (decomposed).

Specific rotatory power $[\alpha]_D: +30.13°$ (C=0.292, chloroform:methanol=8:2).

NMR (DMSO-d$_6$) δ: 0.89(3H, t, J=7 Hz, $CH_3CH_2$—), 1.32(3H, t, J=7 Hz, $CH_3CH_2$—), 1.87(2H, q, J=7 Hz, $CH_3CH_2$—), 5.27(2H, s, $CH_2O$ or $CH_2N$), 5.41(2H, s, $CH_2N$ or $CH_2O$), 6.43(1H, s, OH), 7.28(1H, s, $C_{14}$—H), 7.30–7.50(2H, m, $C_{11}$—H, $C_{12}$—H), 8.02(1H, d, J=10 Hz, $C_9$—H).

Elemental analysis: Calculated for $C_{22}H_{20}N_2O_5 \cdot H_2O$: C, 64.38; H, 5.40; N, 6.82. Found: C, 64.38; H, 5.31; N, 6.62.

REFERENTIAL EXAMPLE 6

(±)-Camptothecin

A reaction mixture, which had been obtained by adding 250 mg of the compound (Ic) obtained in Example 4 and 240 mg of N-(o-aminobenzylidene)-p-toluidine (XVI) to 20 ml of toluene, was heated with stirring for 30 minutes by means of a Dean-Stark apparatus. Three milligrams of p-toluenesulfonic acid were then added and the resulting mixture was heated with stirring for additional 2.5 hours. After allowing the reaction mixture to cool down, precipitated crystals were collected by filtration. After washing them with acetone, they were dried to obtain yellowish powder. Upon recrystallization of the powder from a mixed solvent of acetonitrile and methanol, 230 mg of the title compound was obtained as yellowish crystalline powder.

Melting point: 265°–272° C. (decomposed).

NMR (DMSO-d$_6$) δ: 0.90(3H, t, J=7 Hz, $CH_3CH_2$—), 1.90(2H, q, J=7.5 Hz, $CH_3CH_2$—), 5.32(2H, s, $CH_2N$ or $CH_2O$), 5.44(2H, s, $CH_2O$ or $CH_2N$), 7.40(1H, s, $C_4$—H), 7.60–8.40(4H, m, Ar), 8.74(1H, s, $C_7$—H).

IR $\nu_{max}^{KBr}$ cm$^{-1}$: 3440, 1750, 1660, 1590.

Elemental analysis: Calculated for $C_{20}H_{16}N_2O_4$: C, 68.96; H, 4.63; N, 8.04. Found: C, 68.81; H, 4.61; N, 7.98.

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A pyranoindolizine derivative represented by the following general formula (I):

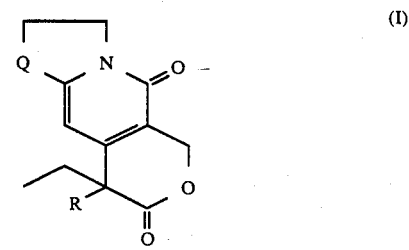

wherein R is a hydrogen atom or hydroxyl group and Q is >C=O or

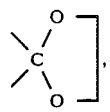
with a proviso that Q is other than >C=O when R is a hydrogen atom.
2. A pyranoindolizine derivative represented by the following formula (I*b):
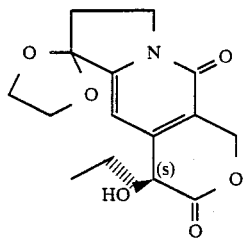
3. A pyranoindolizine derivative represented by the following formula (I*c):
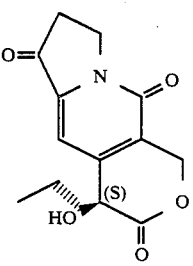
* * * * *